(12) United States Patent
Khairkhahan et al.

(10) Patent No.: US 7,399,271 B2
(45) Date of Patent: *Jul. 15, 2008

(54) VENTRICULAR PARTITIONING DEVICE

(75) Inventors: Alexander Khairkhahan, Palo Alto, CA (US); Serjan D. Nikolic, Los Altos, CA (US); Branislav Radovancevic, Houston, TX (US); Hugh R. Sharkey, Palomar Park, CA (US)

(73) Assignee: CardioKinetix, Inc., Redwood City, CA (US)

( * ) Notice: Subject to any disclaimer, the term of this patent is extended or adjusted under 35 U.S.C. 154(b) by 779 days.

This patent is subject to a terminal disclaimer.

(21) Appl. No.: 10/754,182

(22) Filed: Jan. 9, 2004

(65) Prior Publication Data

US 2005/0154252 A1 Jul. 14, 2005

(51) Int. Cl.
*A61F 2/00* (2006.01)
(52) U.S. Cl. ............................................. 600/16; 600/37
(58) Field of Classification Search .................... 600/16, 600/37
See application file for complete search history.

(56) References Cited

U.S. PATENT DOCUMENTS

| | | | |
|---|---|---|---|
| 3,874,388 A | 4/1975 | King et al. |
| 4,007,743 A | 2/1977 | Blake |
| 4,425,908 A | 1/1984 | Simon |
| 4,619,246 A | 10/1986 | Molgaard-Nielsen et al. |
| 4,710,192 A | 12/1987 | Liotta et al. |
| 4,832,055 A | 5/1989 | Palestrant |
| 4,917,089 A | 4/1990 | Sideris |
| 5,104,399 A | 4/1992 | Lazarus |
| 5,192,301 A | 3/1993 | Kamiya et al. |
| 5,192,314 A | 3/1993 | Daskalakis et al. |
| 5,375,612 A | 12/1994 | Cottenceau et al. |
| 5,385,156 A | 1/1995 | Oliva |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |

(Continued)

FOREIGN PATENT DOCUMENTS

WO  WO 00/27292  5/2000

(Continued)

OTHER PUBLICATIONS

International Search Report and Written Opinion for PCT/US2004/014782 mailed Sep. 21, 2004.

(Continued)

*Primary Examiner*—George R. Evanisko
(74) *Attorney, Agent, or Firm*—Shay Glenn LLP

(57) ABSTRACT

This invention is directed to a partitioning device for separating a patient's heart chamber into a productive portion and a non-productive portion. The device is particularly suitable for treating patients with congestive heart failure. The partitioning device has a reinforced, expandable membrane which separates the productive and non-productive portions of the heart chamber and a support or spacing member extending between the reinforced membrane and the wall of the patient's heart chamber. The support or spacing member has a non-traumatic distal end to engage the ventricular wall.

27 Claims, 5 Drawing Sheets

U.S. PATENT DOCUMENTS

| | | |
|---|---|---|
| 5,549,621 A | 8/1996 | Bessler et al. |
| 5,578,069 A | 11/1996 | Miner, II |
| 5,634,936 A | 6/1997 | Linden et al. |
| 5,634,942 A | 6/1997 | Chevillon et al. |
| 5,702,343 A | 12/1997 | Alferness |
| 5,709,707 A | 1/1998 | Lock et al. |
| 5,791,231 A | 8/1998 | Cohn et al. |
| 5,797,849 A | 8/1998 | Vesely et al. |
| 5,797,960 A | 8/1998 | Stevens et al. |
| 5,829,447 A | 11/1998 | Stevens et al. |
| 5,833,698 A | 11/1998 | Hinchliffe et al. |
| 5,836,968 A | 11/1998 | Simon et al. |
| 5,843,170 A | 12/1998 | Ahn |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,045,497 A | 4/2000 | Schweich et al. |
| 6,059,715 A | 5/2000 | Schweich et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,152,144 A | 11/2000 | Lesh et al. |
| 6,161,543 A | 12/2000 | Cox et al. |
| 6,193,731 B1 | 2/2001 | Oppelt et al. |
| 6,221,092 B1 | 4/2001 | Koike et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,228 B1 | 11/2002 | Norred |
| 6,506,204 B2 | 1/2003 | Mazzocchi |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,592,608 B2 | 7/2003 | Fisher et al. |
| 6,652,555 B1 | 11/2003 | VanTassel et al. |
| 6,685,627 B2 | 2/2004 | Jayaraman |
| 6,852,076 B2 | 2/2005 | Nikolic et al. |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0188170 A1 | 12/2002 | Santamore et al. |
| 2003/0050682 A1 | 3/2003 | Sharkey et al. |
| 2003/0050685 A1 | 3/2003 | Nikolic et al. |
| 2003/0105384 A1 | 6/2003 | Sharkey et al. |
| 2003/0109770 A1 | 6/2003 | Sharkey et al. |
| 2003/0120337 A1 | 6/2003 | Van Tassel et al. |
| 2003/0149333 A1 | 8/2003 | Alferness |
| 2003/0220667 A1 | 11/2003 | Van Der Burg et al. |
| 2004/0002626 A1 | 1/2004 | Feld et al. |
| 2004/0064014 A1 | 4/2004 | Melvin et al. |
| 2004/0260331 A1 | 12/2004 | D'Aquanni et al. |
| 2004/0267378 A1 | 12/2004 | Gazi et al. |
| 2005/0015109 A1* | 1/2005 | Lichtenstein ................ 606/200 |
| 2005/0113861 A1 | 5/2005 | Corcoran et al. |
| 2005/0177180 A1 | 8/2005 | Kaganov et al. |
| 2005/0197716 A1 | 9/2005 | Sharkey et al. |
| 2005/0216052 A1 | 9/2005 | Mazzocchi et al. |
| 2006/0014998 A1 | 1/2006 | Sharkey et al. |
| 2006/0030881 A1 | 2/2006 | Sharkey et al. |

FOREIGN PATENT DOCUMENTS

| | | |
|---|---|---|
| WO | WO 01/30266 | 5/2001 |
| WO | WO 01/78625 | 10/2001 |
| WO | WO 01/78625 A1 | 10/2001 |
| WO | WO 02/30335 | 4/2002 |
| WO | WO 02/071977 A2 | 9/2002 |
| WO | WO 03/007778 | 1/2003 |
| WO | WO 03/007778 A | 1/2003 |
| WO | WO 2004/012629 | 2/2004 |
| WO | WO 2004/012629 A | 2/2004 |
| WO | WO 2004/100803 | 11/2004 |
| WO | WO 2005/007031 | 1/2005 |

OTHER PUBLICATIONS

Tetsuji Kawata et al., "Systolic and Diastolic Function After Patch Reconstruction of Left Ventricular Aneurysms", Ann. Thorac. Surg. 59, pp. 403-407, 1995.

Vincent Dor, "The Treatment of Refractory Ischemic Ventricular Tachycardia by Endoventricular Patch Plasty Reconstruction of the Left Ventricle", Seminars in Thoracic and Cardiovascular Surgery, vol. 9, No. 2, pp. 146-155, Apr. 1997.

Daniel Giorgio Di Mattia et al., "Surgical treatment of left ventricular post-infarction aneurysm with endoventriculoplasty: late clinical and functional results", European Journal of Cardio-thoracic Surgery 15, pp. 413-419, 1999.

T Katsumata et al., "An objective appraisal of partial left ventriculectomy for heart failure", Journal of Congestive Heart Failure and Circular Support, pp. 97-106, 1999.

Vincent Dor, "Surgery for left ventricular aneurysm", Current Opinion in Cardiology, Current Science, pp. 773-780, 1990.

Vincent Dor et al., "Ventricular remodeling in coronary artery disease", Current Opinion in Cardiology, Rapid Science Publishers, pp. 533-537, 1997.

AGA Medical Corporation, www.amplatzer.com/products, "The Muscular VSD Occluder" and "The Septal Occluder" device descriptions, Apr. 3, 2002.

Gore Medical, www.goremedical.com, "Helex Septal Occluder" product description, Apr. 3, 2002.

International Search Report and Written Opinion for PCT/US2005/000264 mailed Apr. 26, 2005.

Khairkhahan, et al., U.S. Appl. No. 10/436,959, entitled "System for improving cardiac function," filed May 12, 2003.

Khairkhahan, et al., U.S. Appl. No. 11/151,164, entitled "Peripheral seal for a ventricular partitioning device," filed Jun. 10, 2005.

Sharkey, et al., U.S. Appl. No. 11/199,633, entitled "Method for treating myocardial rupture," filed Aug. 9, 2005.

Khairkhahan, et al; U.S. Appl. No. 11/801,075, entitled "System for improving cardiac function," filed May 7, 2007.

Khairkhahan et al; U.S. Appl. No. 11/800,998, entitled "System for improving cardiac function," filed May 7, 2007.

Nikolic et al; U.S. Appl. No. 11/640,469, entitled "Cardiac device and methods of use thereof," filed Dec. 14, 2006.

Khairkhahan et al; U.S. Appl. No. 11/860,438 entitled "Laminar ventricular partitioning device," filed Sep. 24, 2007.

* cited by examiner

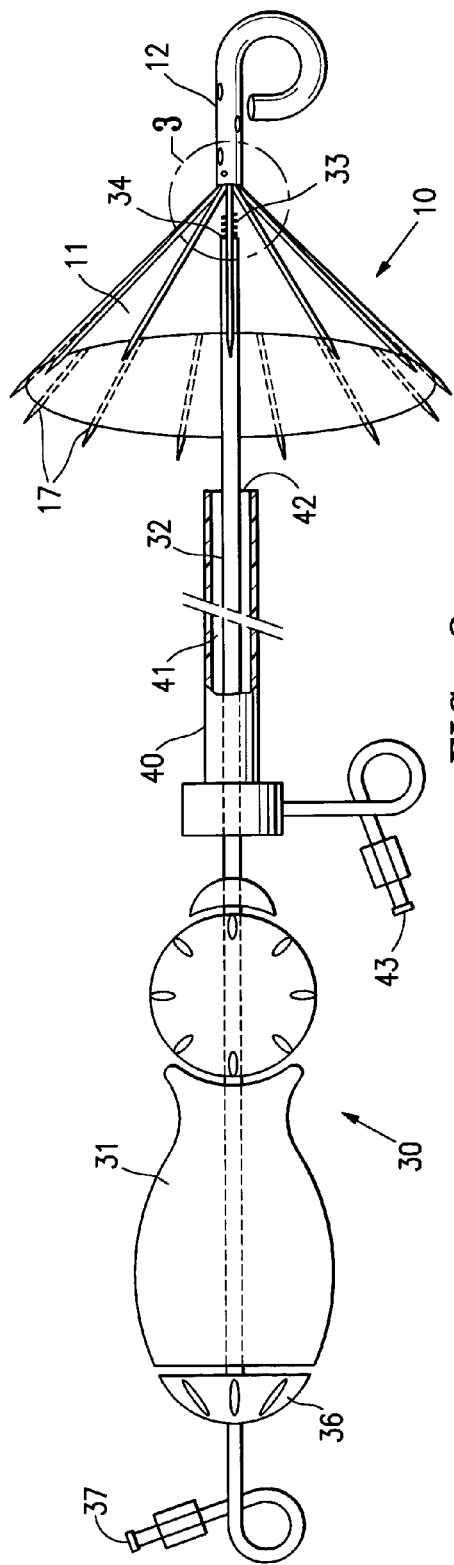
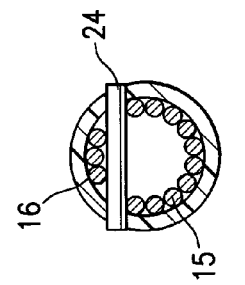
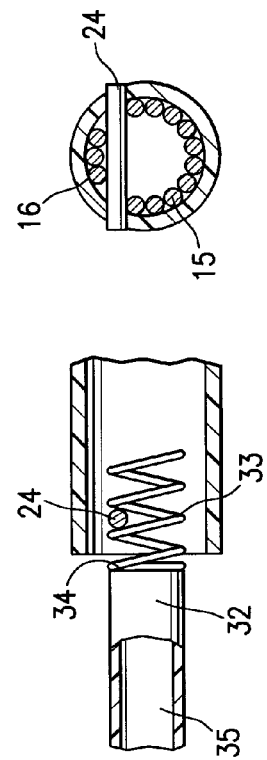
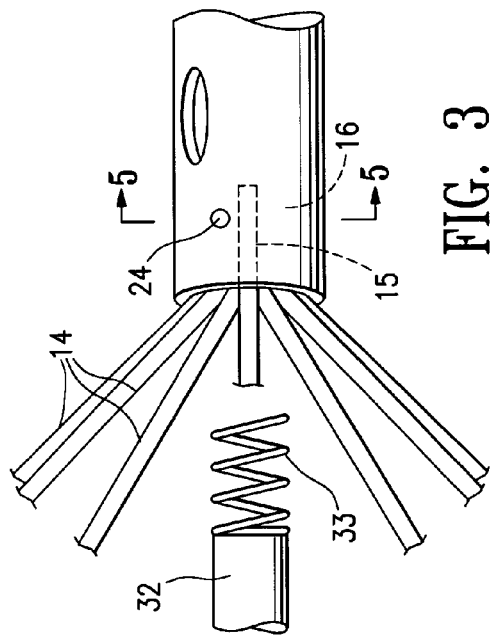

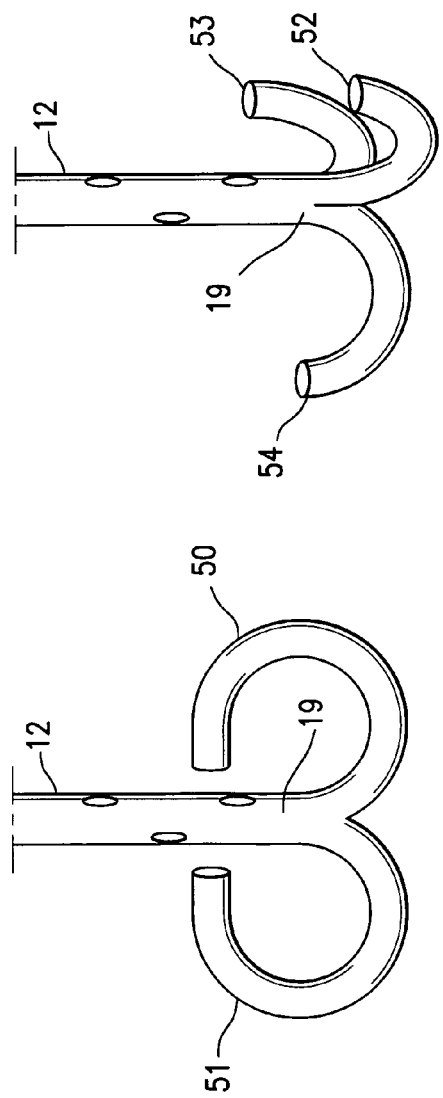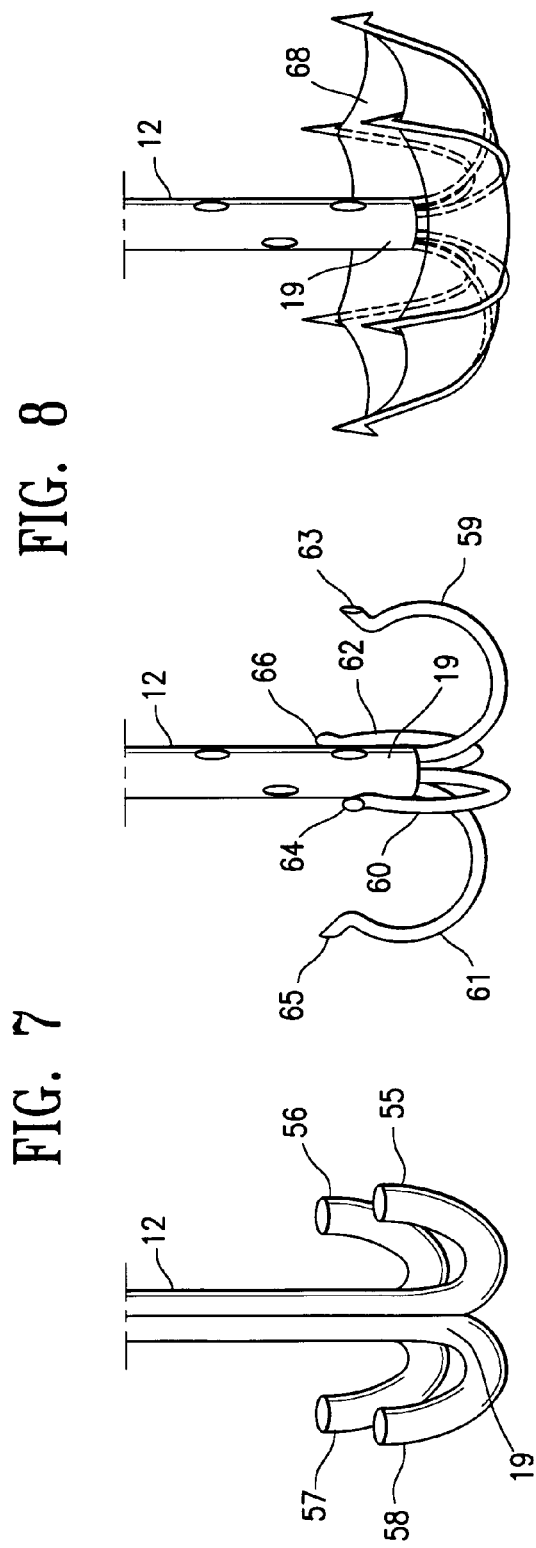

VENTRICULAR PARTITIONING DEVICE

FIELD OF THE INVENTION

The present invention relates generally to the field of treating congestive heart failure and more specifically, to a device and method for partitioning a patient's heart chamber and a system for delivering the treatment device.

BACKGROUND OF THE INVENTION

Congestive heart failure (CHF) is characterized by a progressive enlargement of the heart, particularly the left ventricle and is a major cause of death and disability in the United States. Approximately 500,000 cases occur annually in the U.S. alone. As the patient's heart enlarges, it cannot efficiently pump blood forward with each heart beat. In time, the heart becomes so enlarged the heart cannot adequately supply blood to the body. Even in healthy hearts only a certain percentage of the blood in a patient's left ventricle is pumped out or ejected from the chamber during each stroke of the heart. The pumped percentage, commonly referred to as the "ejection fraction", is typically about sixty percent for a healthy heart. A patient with congestive heart failure can have an ejection fraction of less than 40% and sometimes lower. As a result of the low ejection fraction, a patient With congestive heart failure is fatigued, unable to perform even simple tasks requiring exertion and experiences pain and discomfort. Further, as the heart enlarges, the internal heart valves such as the mitral valve, cannot adequately close. An incompetent mitral valve allows regurgitation of blood from the left ventricle back into the left atrium, further reducing the heart's ability to pump blood forewardly.

Congestive heart failure can result from a variety of conditions, including viral infections, incompetent heart valves (e.g. mitral valve), ischemic conditions in the heart wall or a combination of these conditions. Prolonged ischemia and occlusion of coronary arteries can result in myocardial tissue in the ventricular wall dying and becoming scar tissue. Once the myocardial tissue dies, it is less contractile (sometimes non-contractile) and no longer contributes to the pumping action of the heart. It is referred to as hypokinetic. As the disease progresses, a local area of compromised myocardium may bulge out during the heart contractions, further decreasing the heart's ability to pump blood and further reducing the ejection fraction. In this instance, the heart wall is referred to as dyskinetic or akinetic. The dyskinetic region of the heart wall may stretch and eventually form an aneurysmic bulge.

Patients suffering from congestive heart failure are commonly grouped into four classes, Classes I, II, III and IV. In the early stages, Classes I and II, drug therapy is presently the most commonly prescribed treatment. Drug therapy typically treats the symptoms of the disease and may slow the progression of the disease, but it can not cure the disease. Presently, the only permanent treatment for congestive heart disease is heart transplantation, but heart transplant procedures are very risky, extremely invasive and expensive and are performed on a small percentage of patients. Many patient's do not qualify for heart transplant for failure to meet any one of a number of qualifying criteria, and, Furthermore, there are not enough hearts available for transplant to meet the needs of CHF patients who do qualify.

Substantial effort has been made to find alternative treatments for congestive heart disease. For example, surgical procedures have been developed to dissect and remove weakened portions of the ventricular wall in order to reduce heart volume. This procedure is highly invasive, risky and expensive and is commonly only done in conjunction with other procedures (such as heart valve replacement or coronary artery by-pass graft). Additionally, the surgical treatment is usually limited to Class IV patients and, accordingly, is not an option for patients facing ineffective drug treatment prior to Class IV. Finally, if the procedure fails, emergency heart transplant is the only presently available option.

Other efforts to treat CHF include the use of an elastic support, such as an artificial elastic sock placed around the heart to prevent further deleterious remodeling.

Additionally, mechanical assist devices have been developed as intermediate procedures for treating congestive heart disease. Such devices include left ventricular assist devices and total artificial hearts. A left ventricular assist device includes a mechanical pump for increasing blood flow from the left ventricle into the aorta. Total artificial heart devices, such as the Jarvik heart, are usually used only as temporary measures while a patient awaits a donor heart for transplant.

Recently, improvements have been made in treating patient's with CHF by implanting pacing leads in both sides of the heart in order to coordinate the contraction of both ventricles of the heart. This technique has been shown to improve hemodynamic performance and can result in increased ejection fraction from the right ventricle to the patient's lungs and the ejection fraction from the left ventricle to the patient's aorta. While this procedure has been found to be successful in providing some relief from CHF symtoms and slowed the progression of the disease, it has not been able to stop the disease.

SUMMARY OF INVENTION

The present invention is directed to a ventricular partitioning device and method of employing the device in the treatment of a patient with congestive heart failure. Specifically, the ventricular chamber of the CHF patient is partitioned by the device so as to reduce its total volume and to reduce the stress applied to the heart and, as a result, improve the ejection fraction thereof.

A ventricular partitioning device embodying features of the invention has a reinforced membrane component, preferably self expanding, which is configured to partition the patient's ventricular heart chamber into a main productive portion and a secondary non-productive portion, and a support or spacing component extending from the distal side of the reinforced membrane for non-traumatically engaging a region of the patient's ventricular wall defining in part the secondary non-productive portion to space a central portion of the reinforced membrane from the heart wall. The partitioning device preferably includes a centrally located hub secured to the reinforced membrane. The partitioning membrane of the device may be reinforced by a radially expandable frame component formed of a plurality of ribs.

The ribs of the expandable frame have distal ends secured to the central hub, preferably secured to facilitate abduction of the free proximal ends of the ribs away from a centerline axis. The distal ends of the ribs may be pivotally mounted or formed of material such as superelastic NiTi alloy which allow for compressing the ribs into a contracted configuration and when released allow for their self expansion. The ribs also have free proximal ends configured to engage and preferably penetrate the tissue of the heart wall so as to secure the peripheral edge of the membrane to the heart wall and fix the position of the membrane with respect thereto. The free proximal ends of the ribs may have tissue penetrating tips such as barbs or hooks. The partitioning membrane is secured to the ribs of the expandable frame, preferably on the proximal or pressure side of the expandable frame.

The supporting component or stem of the device has a length configured to extend to the heart wall (typically about 5 mm to about 50 mm, preferably about 15 to about 35 mm), to support and space the membrane from the heart wall. While only one supporting component or stem is described herein, a plurality of such components may be utilized. The supporting component or stem may have at least one inner lumen extending therein for delivery of therapeutic or diagnostic agents through the ports provided along the length thereof. The stem is provided with one or more flexible bumper-type elements on its distal end to non-traumatically engage the weakened ventricular wall and maintain the reinforced membrane, preferably the central portion thereof, spaced a desired distance from the weakened ventricular wall.

The partitioning membrane in the expanded configuration has radial dimensions from about 10 to about 160 mm, preferably about 50 to about 100 mm, as measured from the center line axis.

The partitioning device may be delivered percutaneously or intraoperatively. It is relatively easy to install and provides substantial improvement in the ejection fraction of the patient's heart chamber. These and other advantages of the invention will become more apparent from the following detailed description of the invention and the accompanying exemplary drawings.

BRIEF DESCRIPTION OF THE DRAWINGS

FIG. 2 is an elevational view of a delivery system for the partitioning device shown in FIG. 1

FIG. 3 is an enlarged view of the encircled region 3-3 shown in FIG. 2.

FIG. 4 is a simplified view with parts removed similar to that shown in FIG. 3 with the delivery catheter connected to the partitioning device.

FIG. 5 is an end view of the hub which is secured in the proximal end of the stem of the partitioning device shown in FIG. 1.

FIG. 7 is a schematic perspective view of an alternative design embodying features of the invention with a pair of bumper elements on the distal end of the stem of the partitioning device.

FIG. 8 is a schematic perspective view of another alternative design embodying features of the invention with three bumper elements on the distal end of the stem of the partitioning device.

FIG. 9 is a schematic perspective view of another alternative design embodying features of the invention with four bumper elements on the distal end of the stem of the partitioning device.

FIG. 10 is a schematic perspective view of a fourth alternative design embodying features of the invention with a plurality of bumper elements on the distal end of the stem of the device provided with hooks which fix the end to the interior surface of the patient's ventricular wall.

FIG. 11 is a schematic perspective view of another alternative design embodying features of the invention with a membrane underlying a plurality of bumper elements on the distal end of the stem of the partitioning device.

DETAILED DESCRIPTION OF EMBODIMENTS OF THE INVENTION

Figure 1:
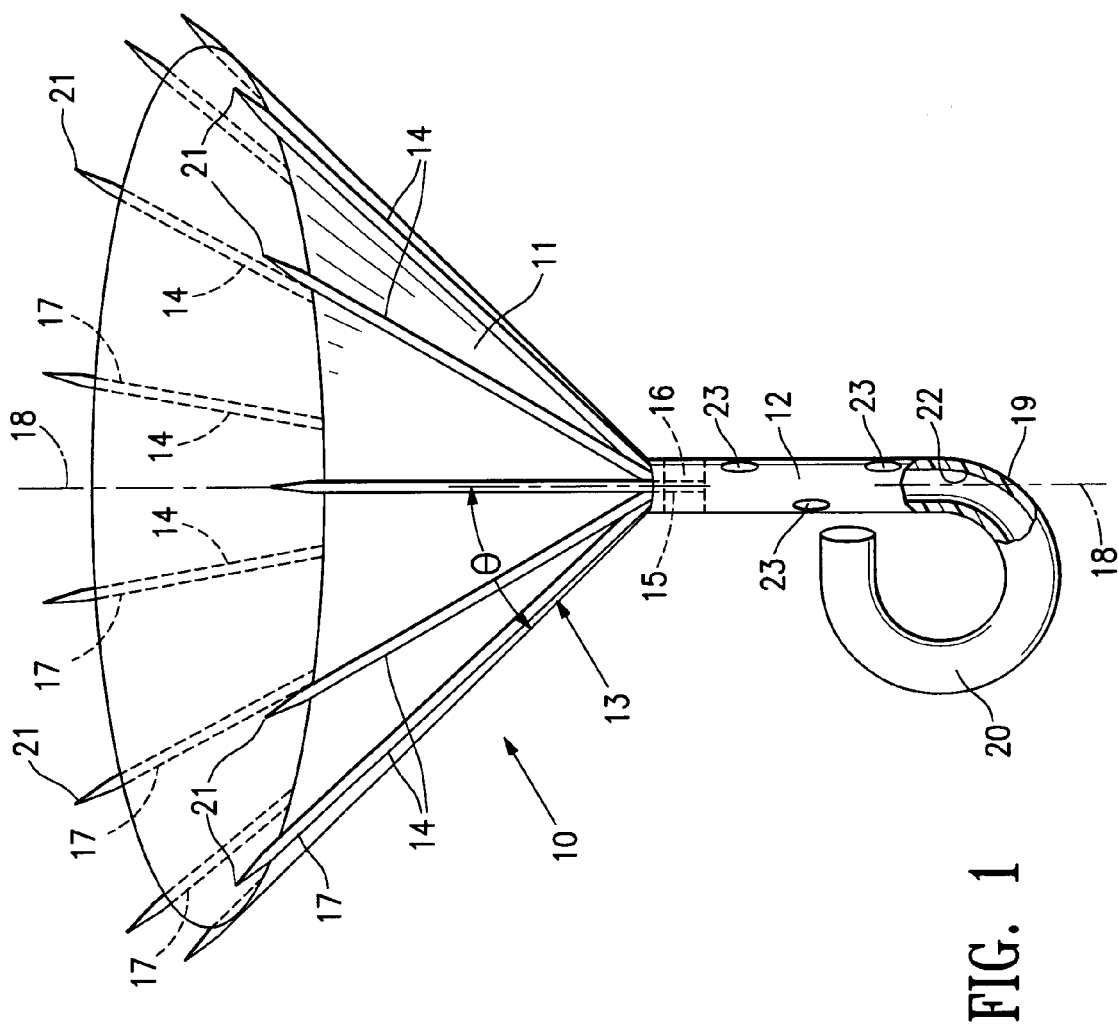
FIG. 1 is a schematic perspective view of a ventricular partitioning device embodying features of the invention.

FIGS. 1-5 illustrate a partitioning device 10 which embodies features of the invention and which includes a partitioning membrane 11, a stem 12 and a radially expandable reinforcing frame 13 formed of a plurality of ribs 14. Preferably the membrane 11 is secured to the proximal or pressure side of the frame 13 as shown in FIG. 1. The distal ends 15 of the ribs 14 are secured to the central hub 16 and the proximal ends 17 of the ribs 14 are unsecured and are configured to radially extend away from a center line axis 18 which extends through the hub 16. Radial expansion of the free proximal ends 17 unfurls the membrane 11 secured to the frame 13 so that the membrane presents a relatively smooth pressure side surface. Stem 12 extends distally from the hub 16 and has a distal end 19 which has a flexible, J-shape bumper element 20 to provide a yielding engagement with a heart wall when deployed within a patient's heart chamber. The frame 13 and attached membrane 11 are collapsible toward the centerline axis 18 for delivery through a catheter.

The proximal or free ends 17 of ribs 14 are provided with sharp tip elements 21 which are configured to hold the frame 13 and the membrane 11 secured thereto in a deployed position within the patient's heart chamber. Preferably, the sharp tip elements 21 of the frame 13 penetrate into tissue of the patient's heart wall in order to secure the reinforced membrane 11 so as to partition the ventricular chamber in a desired manner.

As shown in FIG. 1, the stem 12 is provided with an inner lumen 22 for delivery of fluid to the non-operative portion of the ventricular chamber and discharge ports 23 are provided in the stem. The hub 16 is secured within the inner lumen 22 in the proximal end of stem 12 suitable means such as a friction fit, an adhesive bond or a pin. The hub 16 has a deployment pin 24, as shown in FIG. 5, which as will be described later allows the partitioning device 10 to be deployed within the patient's heart chamber and released from a delivery system used to place the device. The distal ends of the reinforcing ribs 14 are secured to the hub 16 in a suitable manner. They may be secured to the surface defining the inner lumen or the hub may be provided with channels or bores in the wall of the hub into which the distal ends of the ribs may be secured. The ribs 14 are preshaped so that when not constrained (as shown in FIGS. 1 and 2), the free proximal ends 17 thereof expand to a desired angular displacement (θ) away from a center line axis 18 which is about 20° to about 90°, preferably about 50° to about 80°.

FIGS. 2-4 illustrate a suitable delivery system 30 with a partitioning component device 10 as shown in FIG. 1. The delivery system 30 includes a control handle 31 with a delivery catheter 32 having a deploying coil screw 33 secured to the distal end 34 for releasing the partitioning device 10 from the delivery system 30. The delivery catheter 32 has a an inner lumen 35 through which therapeutic or diagnostic fluids may be delivered. The delivery catheter 32 extends through the handle 31 and the proximal end of the catheter 32 is secured to torquing knob 36 to allow rotation of the catheter by rotating knob 36. An injection port 37 is provided in fluid communication with the delivery catheter 32 for injecting therapeutic or diagnostic fluids through the inner lumen 35.

Figure 6:
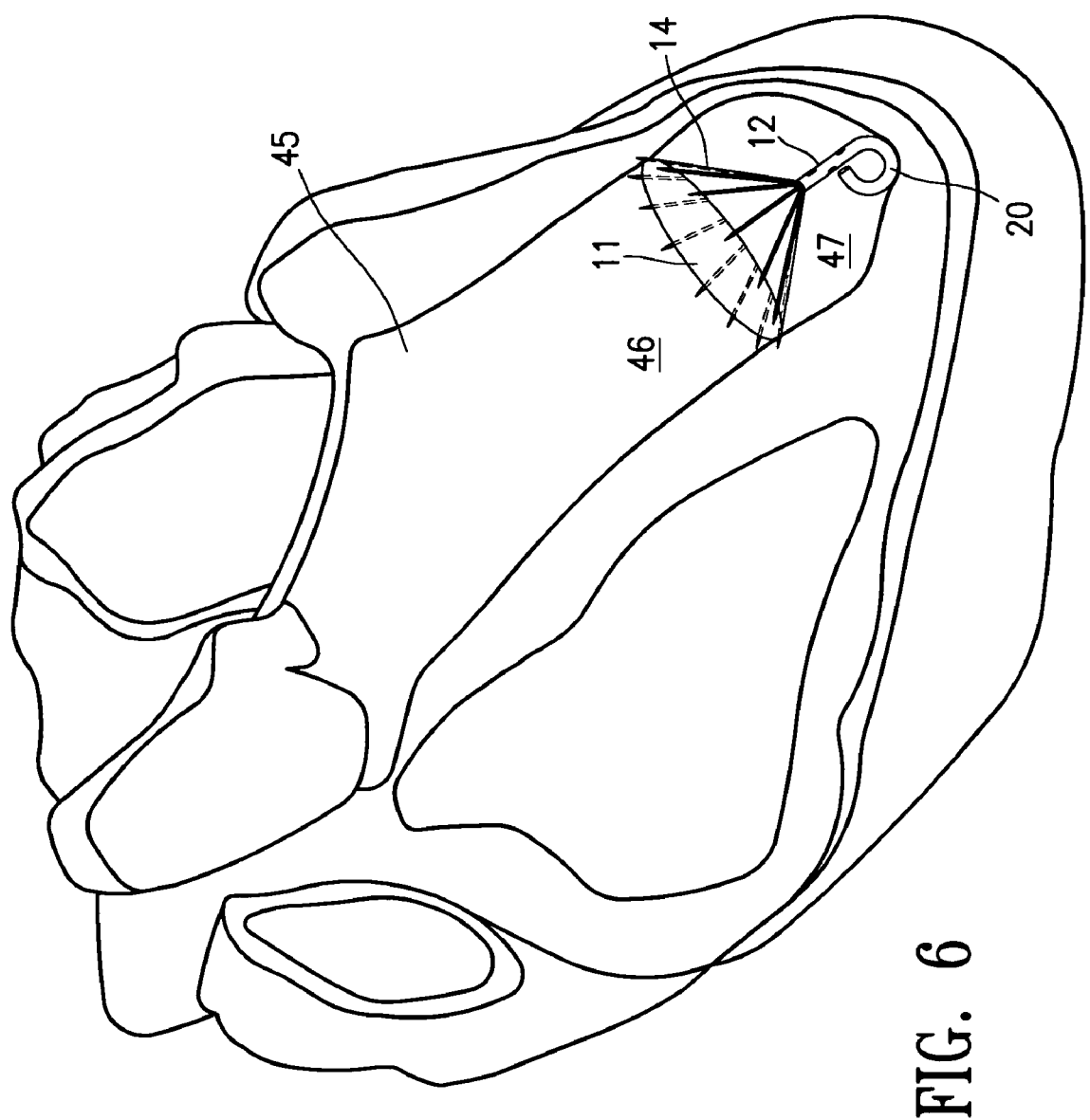
FIG. 6 is a schematic view of a patient's left ventricular chamber illustrating the partitioning device shown in FIG. 1 disposed within the chamber separating a working portion of the chamber from an non-working portion of the chamber.

The delivery system 30 may be introduced into a patient's body through guiding catheter or cannula 40 which has an inner lumen 41. A radiopaque marker (not shown) may be provided on the distal end of the guiding catheter 40 to aid in fluoroscopically guiding the catheter to the desired location. The partitioning device 10 is slidably disposed within the inner lumen 41 with the free proximal ends 17 of the ribs 14 in a constricted configuration. The guiding catheter 40 is percutaneously introduced in a conventional fashion into the patient's vasculature and advanced therein until the distal end 42 of the guiding catheter 40 is position close to the desired location for the partitioning device 10 within the patient's heart chamber such as the left ventricle. The delivery system 30 is advanced distally within the inner lumen 41 until the J-shaped bumper 20 extends out the distal end 42 of the guiding catheter 40 and engages the ventricular wall. With the delivery system 30 held in place and the bumper 20 engaging the ventricular wall, the guide catheter 40 is pulled proximally until the free ends 17 of ribs 14 are released from the distal end 42 so that anchoring tip elements 21 on the free proximal ends 17 of ribs 14 penetrate into tissue of the patient's heart wall as shown in FIG. 6 to secure the partitioning device 10 within the patient's heart chamber. With the partitioning device 10 properly positioned within the heart chamber, the delivery catheter 32 is rotated counter-clockwise to disengage the delivery system 30 from the hub 16. Upon the counter-clockwise rotation of the delivery catheter 32, the helical coil screw 33 attached to the distal end 34 of the delivery catheter 32 rides on the deployment pin 24 secured within the inner lumen 22 of the hub 16. The delivery system 30 and the guide catheter 40 may then be removed from the patient. The proximal end of the guide catheter 40 is provided with an injection port 43 to inject therapeutic or diagnostic fluids through the inner lumen 41.

FIG. 6 illustrates the placement of partitioning device 10 within a patient's left ventricle 45. The membrane 11 secured to the proximal side of ribs 14 partitions the patient's heart chamber 45 into a main productive or operational portion 46 and a secondary, essentially non-productive portion 47. The operational portion 46 is much smaller than the original ventricular chamber 45 and provides for an improved ejection fraction. The partitioning increases the ejection fraction and provides an improvement in blood flow. Over time, the non-productive portion 47 fills initially with thrombus and subsequently cellular growth. Bio-resorbable fillers such as polylactic acid, polyglycolic acid, polycaprolactone and copolymers and blends may be employed to fill the non-productive portion 47. Fillers may be suitably supplied in a suitable solvent such as DMSO. Other materials which accelerate tissue growth may be deployed in the non-productive portion 47.

FIGS. 7-12 illustrate distal ends 19 of the partitioning devices having alternative bumper elements for providing non-traumatic contact with a weakened ventricular wall. In FIG. 7 the distal end 19 of stem 12 has a pair of J-shaped bumpers 50 and 51. In FIG. 8 the distal end 19 has three J-shaped bumpers 52, 53 and 54. FIG. 9 illustrates a distal end 19 having four J-shaped bumpers 55, 56, 57 and 58. FIG. 10 depicts a slight change, where the distal end 19 has four wire J-shaped bumpers 59-62 with sharp tips 63-66 for securing the ends of the bumpers in heart tissue. A further alternative is illustrated in FIG. 11 where a membrane 68 is applied to the J-shaped bumpers In FIG. 12, the distal end 19 of stem 12 is provided with a coiled bumper 70 for engaging a ventricular wall.

Figure 13:
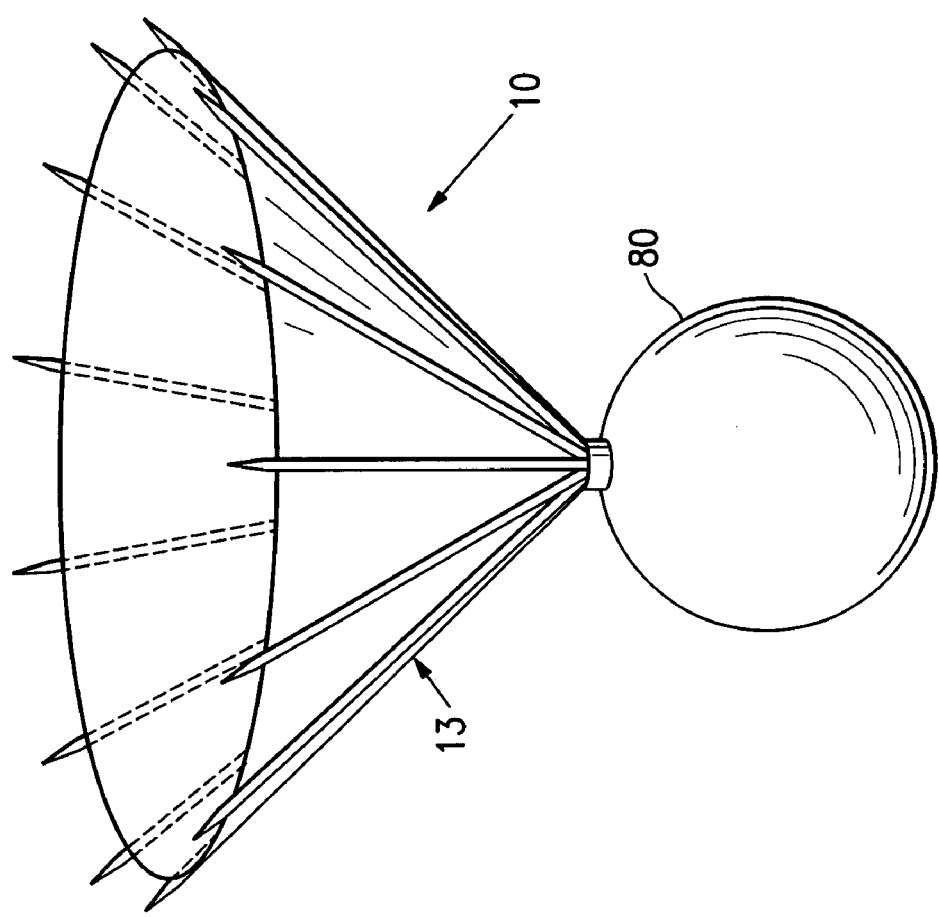
FIG. 13 is a schematic perspective view of yet another alternative design embodying features of the invention with an inflatable balloon secured to the underside of the partitioning device to space and support the partitioning device from the heart wall.
Figure 12:
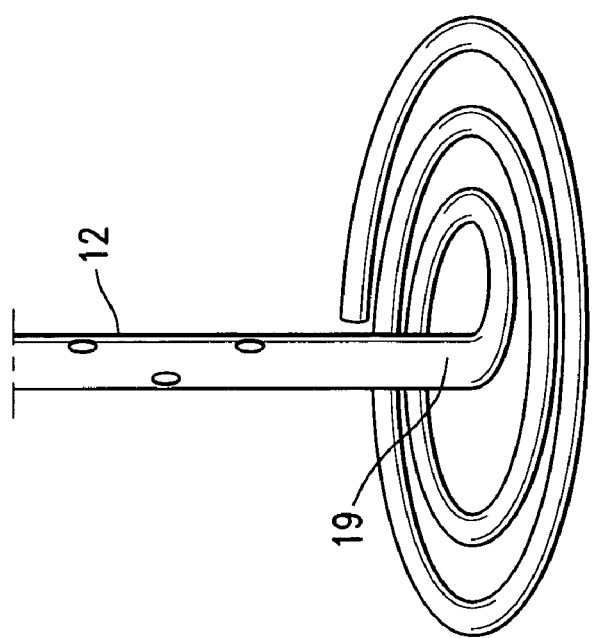
FIG. 12 is a schematic perspective view of another alternative design embodying features of the invention with a helical coil bumper element on the distal end of the stem of the partitioning device.

Another modification is shown in FIG. 13 wherein an inflatable balloon 80 is provided on the distal side of the frame 13 to support and space the partitioning device 10 from a patient's ventricular wall in lieu of the stem with flexible bumpers, as shown in the partitioning devices previously described.

The ribs 14 of the partitioning device have a length of about 1 to about 8 cm, preferably, about 1.5 to about 4 cm for most left ventricle deployments. To assist in properly locating the device during advancement and placement thereof into a patient's heart chamber, the distal extremity of one or more of the ribs and/or the stem may be provided with markers at desirable locations that provide enhanced visualization by eye, by ultrasound, by X-ray, or other imaging or visualization means. Radiopaque markers may be made with, for example, stainless steel, platinum, gold, iridium, tantalum, tungsten, silver, rhodium, nickel, bismuth, other radiopaque metals, alloys and oxides of these metals.

The membrane 11 may be formed of suitable biocompatitble polymeric material which include ePTFE (expanded polytetrafluoroethylene), Nylon, PET (polyethylene terephthalate) and polyesters such as Hytrel. The membrane 11 is preferably foraminous in nature to facilitate tissue in growth after deployment within the patient's heart. The delivery catheter and the guiding catheter may be formed of suitable high strength polymeric material such as PEEK (polyetheretherketone), polycarbonate, PET, Nylon, and the like. Braided composite shafts may also be employed. To the extent not otherwise described herein, the various components of the partitioning device and delivery system may be formed of conventional materials and in a conventional manner as will be appreciated by those skilled in the art.

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

Terms such a "element", "member", "device", "section", "portion", "steps", "means" and words of similar import when used herein shall not be construed as invoking the provisions of 35 U.S.C. §112(6) unless the following claims expressly use the terms "means" followed by a particular function without specific structure or "step" followed by a particular function without specific action. All patents and patent applications referred to above are hereby incorporated by reference in their entirety. Accordingly, it is not intended that the invention be limited, except as by the appended claims.

What is claimed is:

1. A partitioning apparatus for a patient's heart chamber to improve cardiac ejection fraction, comprising:
   a. a central hub component;
   b. an expandable frame component having a plurality of ribs with free proximal ends and distal ends secured to the central hub;
   c. a membrane component secured to the expandable frame ribs which limits the radial expansion of the free proximal ends of the ribs to less than about 90° from a center line axis, wherein the membrane component is configured to partition the patient's ventricle and withstand repeated ventricular contractions; and d. a support component extending from a distal side of the frame comprising an elongated stem and a bumper, wherein the bumper is configured to non-traumatically engage a region of the patient's ventricular wall defining in part the heart chamber being partitioned.

2. The partitioning apparatus of claim 1 wherein the bumper has at least one resilient member to non-traumatically engage the region of the patient's ventricular wall.

3. The partitioning apparatus of claim 2 wherein the at least one resilient member has a J-shape.

4. The partitioning apparatus of claim 2 wherein the bumper has a helical coil shape.

5. The partitioning apparatus of claim 1 wherein the support component is an inflatable member.

6. The partitioning apparatus of claim 1 wherein the membrane component is secured to the proximal side of the ribs.

7. The partitioning apparatus of claim 1 wherein the membrane component is secured to the distal side of the ribs.

8. The device of claim 1, wherein the membrane component in the expanded configuration has a radial dimension from about 50 mm to about 100 mm from the center line axis.

9. The device of claim 1, wherein the stem extends distally along the center line axis.

10. The device of claim 1, wherein the bumper extends in a plane substantially perpendicular to the stem.

11. The device of claim 1, wherein the stem extends between about 5 mm and about 50 mm from the distal side of the expandable frame component.

12. The device of claim 1, wherein the stem extends between about 15 mm and about 35 mm from the distal side of the expandable frame component.

13. The device of claim 1, wherein the bumper comprises a loop.

14. The device of claim 1, wherein the stem comprises an internal lumen and one or more ports through which a diagnostic or therapeutic agent may be delivered.

15. A device for treating a patient with CHF by partitioning a heart chamber thereof, comprising:
   a. a central hub component;
   b. an expandable frame component having a plurality of ribs with distal ends secured to the central hub component and free proximal ends and distal ends secured to the central hub component;
   c. a membrane component secured to the ribs of the expandable frame, wherein the membrane component is configured to partition the patient's ventricle and withstand repeated ventricular contractions; and
   d. a support component comprising an elongated stem and a bumper, wherein the stem extends from the distal side of the expandable frame component, and wherein the bumper extends in a plane substantially perpendicular to the stem and is configured to space the expandable frame component from a ventricular wall and has sufficient give to provide non-traumatic engagement with a weakened portion of the ventricular wall.

16. The device of claim 15 wherein the ribs of the expandable frame component limit the radial expansion of the free proximal ends of the ribs to less than 90°.

17. The device of claim 15 wherein the support component has a proximal end secured to the central hub component and the bumper is secured at the distal end of the stem.

18. The device of claim 17 wherein the flexible bumper of the support component has a J-shape.

19. The device of claim 17 wherein the distal end of the support component has a plurality of J-shape bumpers.

20. The device of claim 15, wherein the membrane component in the expanded configuration has a radial dimension from about 50 mm to about 100 mm from the center line axis.

21. The device of claim 15, wherein the stem extends distally along the center line axis.

22. The device of claim 15, wherein the stem extends between about 5 mm and about 50 mm from the distal side of the expandable frame component.

23. The device of claim 15, wherein the stem extends between about 15 mm and about 35 mm from the distal side of the expandable frame component.

24. The device of claim 15, wherein the bumper extends in plane substantially perpendicularly from the distal end of the center line axis.

25. The device of claim 15, wherein the bumper comprises a loop.

26. The device of claim 15, wherein the stem comprises an internal lumen and one or more ports through which a diagnostic or therapeutic agent may be delivered.

27. A device for treating a patient with CHF by partitioning a heart chamber thereof, comprising:
   a. a central hub;
   b. a frame having a plurality of ribs with distal ends secured to the central hub and free proximal ends and distal ends secured to the central hub;
   c. a membrane secured to the ribs of the frame, wherein the membrane is configured to partition the patient's ventricle and withstand repeated ventricular contractions; and
   d. a support which extends from the distal side of the expandable frame, which is configured to space the expandable frame from a ventricular wall and which has sufficient give to provide non-traumatic engagement with a weakened portion of the ventricular wall, wherein the support comprises an elongated stem and a curved bumper, wherein the elongate stem extends distally along a center line axis, and the bumper extends in a plane substantially perpendicular to the stem.

* * * * *